(12) United States Patent
Arnold et al.

(10) Patent No.: US 6,379,932 B1
(45) Date of Patent: Apr. 30, 2002

(54) SINGLE PRIMER PCR AMPLIFICATION OF RNA

(75) Inventors: Lyle Arnold, Poway; Erik Bjeldanes, Lafyette, both of CA (US); Steve Daniel, The Woodlands, TX (US)

(73) Assignee: Incyte Genomics, Inc., Palo ALto, CA (US)

( * ) Notice: Subject to any disclaimer, the term of this patent is extended or adjusted under 35 U.S.C. 154(b) by 0 days.

(21) Appl. No.: 09/617,578

(22) Filed: Jul. 17, 2000

(51) Int. Cl.[7] .......................... C12P 19/34; C12Q 1/68; G01N 33/00; C07H 21/02; C07H 21/04
(52) U.S. Cl. ....................... 435/91.51; 435/6; 435/91.1; 435/91.2; 436/94; 536/23.1; 536/24.3; 536/24.33
(58) Field of Search .................... 435/6, 91.1, 91.2, 435/183, 91.31, 91.51; 436/94, 501; 536/23.1, 24.3, 24.33, 25.3

(56) References Cited

U.S. PATENT DOCUMENTS 5,262,311 A * 11/1993 Pardee ...................... 435/91.2
5,654,143 A * 8/1997 Mallet et al. .................. 435/6
5,741,640 A * 4/1998 Fuller ............................ 435/6

OTHER PUBLICATIONS

Van Gelder et al., Amplified RNA synthesized from limited quantities of heterogeneous cDNA. Proc. Natl. Acad. Sci. USA 87, 1663–1667, Mar. 1990.*

* cited by examiner

*Primary Examiner*—Ethan C. Whisenant
*Assistant Examiner*—Frank Lu
(74) *Attorney, Agent, or Firm*—Richard Aron Osman

(57) ABSTRACT

The invention provides methods and compositions for amplifying RNA sequences by (a) hybridizing to a target RNA a first primer comprising a 3' target RNA hybridizing sequence and a first 5' defined amplifyable sequence; (b) extending the first primer with a reverse transcriptase to form a first cDNA strand; (c) hybridizing to the first cDNA strand a second primer comprising a 3' random cDNA hybridizing sequence and a second 5' defined amplifyable sequence; (d) extending the second primer with a DNA polymerase to form a second cDNA strand; and (e) amplifying the second cDNA strand with a third primer comprising the first 5' defined amplifyable sequence.

20 Claims, No Drawings

SEQUENCE LISTING

```
<160> NUMBER OF SEQ ID NOS: 6

<210> SEQ ID NO 1
<211> LENGTH: 26
<212> TYPE: DNA
<213> ORGANISM: Artificial Sequence
<220> FEATURE:
<223> OTHER INFORMATION: Description of Artificial  Sequence: Synthetic
      Sequence
<221> NAME/KEY: misc_feature
<222> LOCATION: (1)..(9)
<223> OTHER INFORMATION: note="n signifies v ariable nucleotide"

<400> SEQUENCE: 1
nnnnnnnnng tttcccagtc acgatc                                            26

<210> SEQ ID NO 2
<211> LENGTH: 17
<212> TYPE: DNA
<213> ORGANISM: Artificial Sequence
<220> FEATURE:
<223> OTHER INFORMATION: Description of Artificial  Sequence: Synthetic
      Sequence

<400> SEQUENCE: 2
gtttcccagt cacgatc                                                      17

<210> SEQ ID NO 3
<211> LENGTH: 34
<212> TYPE: DNA
<213> ORGANISM: Artificial Sequence
<220> FEATURE:
<223> OTHER INFORMATION: Description of Artificial  Sequence: Synthetic
      Sequence

<400> SEQUENCE: 3
actcagcgtt gttaccattt tttttttttt tttt                                   34

<210> SEQ ID NO 4
<211> LENGTH: 17
<212> TYPE: DNA
<213> ORGANISM: Artificial Sequence
<220> FEATURE:
<223> OTHER INFORMATION: Description of Artificial  Sequence: Synthetic
      Sequence

<400> SEQUENCE: 4
actcagcgtt gttacca                                                      17

<210> SEQ ID NO 5
<211> LENGTH: 26
<212> TYPE: DNA
<213> ORGANISM: Artificial Sequence
```

-continued

```
<220> FEATURE:
<223> OTHER INFORMATION: Description of Artificial  Sequence: Synthetic
      Sequence
<221> NAME/KEY: misc_feature
<222> LOCATION: (18)..(26)
<223> OTHER INFORMATION: note="n signifies v ariable nucleotide"

<400> SEQUENCE: 5
actcagcgtt gttaccannn nnnnnn                                            26

<210> SEQ ID NO 6
<211> LENGTH: 35
<212> TYPE: DNA
<213> ORGANISM: Artificial Sequence
<220> FEATURE:
<223> OTHER INFORMATION: Description of Artificial  Sequence: Synthetic
      Sequence

<400> SEQUENCE: 6
actcagcgtt gttaccattt tttttttttt ttttv                                  35
```

SINGLE PRIMER PCR AMPLIFICATION OF RNA

FILED OF THE INVENTION

The field of the invention is amplifying RNA.

BACKGROUND

RNA is a frequent starting material for genetic analysis, such as microarray-based diagnostics and sequencing, and a wide variety of methods have been devised to amplify RNA, generally by first copying the RNA to cDNA and then using PCR and/or repeated rounds of transcription to obtain an amplified product. For example, Silver et al. (1992) U.S. Pat. No. 5,104,792; Liang et al. (1997) U.S. Pat. No. 5,599,672; and Shuber (1999) U.S. Pat. No. 5,882,856 describe methods for amplifying RNA. The present invention provides an improved method of amplifying RNA which is adaptable to total RNA input, low quantity input (100 pg or less mRNA) and linear or quantitative PCR amplification.

SUMMARY OF THE INVENTION

The invention provides methods and compositions for amplifying RNA sequences. In one aspect, the invention comprises the steps of:
(a) hybridizing to a target RNA a first primer comprising a 3' target RNA hybridizing sequence and a first 5' defined amplifiable sequence;
(b) extending the first primer with a reverse transcriptase to form a first cDNA strand;
(c) hybridizing to the first cDNA strand a second primer comprising a 3' random EDNA hybridizing sequence and a second 5' defined amplifiable sequence;
(d) extending the second primer with a DNA polymerase to form a second cDNA strand; and
(e) amplifying the second cDNA strand with a third primer comprising the first 5' defined amplifiable sequence.

In one principal embodiment, step (b) yields a heteroduplex of the target RNA and the first cDNA and flier comprises the step of digesting the target RNA of the heteroduplex with a RNase sufficient to permit hybridization of the first cDNA strand with the second primer without a melting step. In various applications, the 3' target RNA hybridizing sequence may be random or nonrandom, such as complementary to a predetermined sequence (e.g. a coding region, a polyA junction, or a polyA tail), and the first and second 5' defined amplifiable sequences may be the same or different. In particular embodiments wherein the first and second 5' defined amplifiable sequences are different, the method further comprises the step of functionally depleting the first primer between steps (b) and (c); step (e) further comprises amplifying the second cDNA strand with a fourth primer comprising the second 5' defined amplifiable sequence; and/or the method further comprises step (D amplifying the amplified cDNA with an excess of either the third or fourth primer to form a predominantly single stranded amplified probe of a predetermined orientation. In particular applications, the method may be practiced in a single tube (homogeneous assay).

In another principal embodiment, the 3' target RNA hybridizing sequence is random; the first and second 5' defined amplifiable sequences are different; and step (b) comprises the step of functionally depleting the first primer to prevent it from hybridizing with the first cDNA strand in subsequent steps.

In aspects of both principal embodiments, interference by the first and/or second primers with the amplification step (e) may be reduced by adding the third and/or fourth primer of step (e) in functional excess of the first and/or second primer; and/or functionally depleting remaining first and second primers between steps (d) and (e).

DESCRIPTION OF SPECIFIC EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more and the term "or" means and/or.

The first step of the disclosed methods comprises (a) hybridizing to a target RNA a first primer comprising a 3' target RNA hybridizing sequence and a first 5' defined amplifiable sequence. A wide variety of target RNAs may be employed, including total cellular RNA, amplified RNA, purified RNA species such as rRNA, tRNA or preferably, mRNA, etc. The fist primer comprises a 3' sequence of length and sequence sufficient to hybridize with the target RNA. Depending on the application, this 3' hybridizing sequence may be random, specific or a combination of random and specific sequences. For example, a primer population comprising random 3' hybridizing sequences provides a "universal" primer set capable of targeting any RNA species. In other embodiments, primers comprising polyT 3' hybridizing sequences may be used to target polyA tails of mRNA; primers comprising predetermined specific sequences may be used to target particular, predetermined RNA species comprising complementary sequences; and primers comprising a random region joined to a wobble nucleotide (A, C or G) joined to a polyT region may be used to target mRNA polyA junctions. The first primer also comprises a first 5' defined amplifiable sequence, which may be any sequences which can be used in the subsequent specific amplification step and preferably comprises a PCRable tag. Suitable reaction conditions for effecting hybridization between the target RNA and first primer are known in the art, readily ascertained empirically, and/or described and/or exemplified herein.

The second step of the methods comprises (b) extending the first primer with a reverse transcriptase to form a first cDNA strand. Depending on the application, an RNAse activity may be present during this step, which can effect the degradation of the original RNA template subsequent to, or coincident with reverse transcription, allowing, for example, priming of the new cDNA strand with the same primer. In a preferred embodiment, the RNAse activity is provided by the reverse transcriptase, such as Moloney Murine Leukemia Virus (MMLV) reverse transcriptase, Avian Myeloblastosis Virus (AMV) reverse transcriptase (both available from Promega, Madison, Wis.), Rous Associated Virus 2 (RAV2) and Human Immunodeficiency Virus 1 (HIV1) reverse transcriptases (both available from Amersham Pharmacia), etc. In applications where the 3' target RNA hybridizing sequence is random and the first and second 5' defined amplifyable sequences are different, RNAse activity is preferably avoided so that second strand cDNA synthesis does not occur in the same reaction mixture. Exemplary suitable reverse transcriptases without RNase activity include MMLV-RT RNase H minus (e.g Promega Catalog #M5301 and #M3682), display THERMO-RT (Display Systems Biotech, Vista Calif.), Strat-Script RT (Stratagene, San Diego, Calif.), etc.

The third step of the methods comprises (c) hybridizing to the first cDNA strand a second primer comprising a 3' random cDNA hybridizing sequence and a second 5' defined amplifiable sequence. Note that depending on the application, the second primer may have the same 3' hybridizing sequence and/or the same 5' defined amplifiable sequences as does the first primer, or one or both sequences may differ; see examples, below. For example, where the first and second 5' defined amplifiable sequences are different, the method may also comprise the step of functionally depleting the first primer between steps (b) and (c). Functional depletion reduces interference of the first primer with the second primer extension reaction and may be effected by any convenient means such as removal (e.g. size exclusion or affinity chromatography), inactivation (e.g. hydrolysis, conjugation, etc.), etc.

The fourth step of the methods comprises (d) extending the second primer with a DNA polymerase to form a second cDNA strand. Suitable DNA polymerases and reaction conditions are known in the art, readily ascertained empirically, and/or described and/or exemplified below.

The fifth step of the method comprises (e) amplifying the second cDNA strand with a third primer comprising the first 5' defined amplifiable sequence. To reduce interference from the first primer, the third primer of step (e) may be added in functional excess of the first primer, and/or remaining first (and/or second primer, if present and distinct from the first) may be functionally depleted between steps (d) and (e). Depending on the particular application, amplification step (e) may employ additional primers and reactions. For example, where the first and second 5' defined amplifiable sequences are different, step (e) may further comprise amplifying the second cDNA strand with a fourth primer comprising the second 5' defined amplifiable sequence. In a more particular embodiment of this application, the method further comprises step (f) amplifying the amplified cDNA with an excess of either the third or fourth primer to form a predominantly single stranded amplified probe of a predetermined orientation.

Preferred applications of the method reduce handling steps, such as wash steps, inherent in prior art methods, preferably to only a single wash step, more preferably to no wash steps wherein the method is practiced continuously, preferably homogenously, and in a single tube (i.e. container or reaction vessel).

The third and fourth primers comprise sequences identical to those of the defined sequence portions of the first and second primers and may contain optional detectable labels at positions other than their 3' termini. The labels may be directly detectable, as in the case of fluorescent or radio labels, or indirectly detectable, as in the case of biotin, nitrophenol, or related labels for which there are high affinity specific binding reagents which contain directly detectable labels and which are used in second binding reactions to measure the presence of the indirect labels.

In a preferred mode, the sequences of the sequence specific portions of the first primer and the second primer are identical. In this mode, the third and fourth primers that are optionally labeled are also identical, such that only two primers become necessary for all amplification and labeling steps. In a further preferred mode, the hybridization temperature of the first primer portion that hybridizes to the mRNA and the second primer portion that hybridizes to the cDNA are between 20° C. and 45° C., and the hybridization temperature of the sequence specific portions of the first and second primers are between 50° C. and 80° C.

In yet other modes of this invention, labeling does not occur during the amplification process, but is done after amplification. In this mode, the amplification products can be labeled by a variety of methods including the incubation of reactive label reagents with sites on the DNA strands that include the terminal hydroxyl group, exocyclic amines of the DNA bases, and the bridging internucleotide phosphate groups. Alternatively, labels may be incorporated by the process of nick-translation employing appropriately labeled nucleotide triphosphates and an appropriate DNA polymerase such as the Klenow fragment.

A wide variety of materials and methods are known in the art for arraying polynucleotides at discrete elements of substrates such as glass, silicon, plastics, nylon membranes, etc., including contact deposition, e.g. U.S. Pat. Nos. 5,807,522; 5,770,151, etc.; photolithography-based methods, e.g. U.S. Pat. Nos. 5,861,242; 5,858,659; 5,856,174; 5,856,101; 5,837,832, etc; flow path-based methods, e.g. U.S. Pat. No. 5,384,261; dip-pen nanolithography-based methods, e.g. Piner, et al., Science Jan. 29, 1999: 661–663, etc.; etc. In a preferred embodiment, the capture polynucleotides are arrayed at corresponding discrete elements in high density, generally at least 100, preferably at least 1000, more preferably at least 10,000, most preferably at least 100,000 discrete elements per square centimeter.

In one principle application of the method, step (b) yields a heteroduplex of the target RNA and the first cDNA and further comprises the step of digesting the target RNA of the heteroduplex with a RNase sufficient to permit hybridization of the first cDNA strand with the second primer without a melting step. In particular embodiments of this application, the first and second 5' defined amplifiable sequences are the same and the 3' target RNA hybridizing sequence is random; the first and second 5' defined amplifiable sequences are the same and the 3' target RNA hybridizing sequence is nonrandom; the first and second 5' defined amplifiable sequences are the same, the 3, target RNA hybridizing sequence is nonrandom and the method is practiced in a single tube; the 3' target RNA hybridizing sequence is nonrandom, the first and second 5' defined amplifiable sequences are different and the method further comprises the step of functionally depleting the first primer between steps (b) and (c); the 3' target RNA hybridizing sequence is nonrandom, the first and second 5' defined amplifiable sequences are different, the method further comprises the step of functionally depleting the first primer between steps (b) and (c) and the method is practiced in a single tube.

In a second principle application of the method, the 3' target RNA hybridizing sequence is random; the first and second 5' defined amplifiable sequences are different; and step (b) comprises the step of functionally depleting the first primer to prevent it from hybridizing with the first cDNA strand in subsequent steps. Exemplary protocols for representative examples of these principle applications are provided below.

EXEMPLARY EXPERIMENTAL PROTOCOLS

EXAMPLE 1

Random Prime from polyA

The cDNA microarrays were made according to U.S. Pat. No. 5,807,522 by Incyte Genomics, Inc. The oligonucleotides were synthesized and purified by Operon Technologies, and used without further purification.

The following oligonucleotide sequences were used in the execution of the example:

| | |
|---|---|
| NNNNNNNNNGTTTCCCAGTCACGATC | (SEQ ID NO:1) |
| GTTTCCCAGTCACGATC | (SEQ ID NO:2) |

The oligonucleotide of SEQ ID NO:1 was used to randomly prime a standard $1^{st}$ strand cDNA reverse transcription reaction using complex polyA purified human mRNA as template. M-MLV (RNase H+) reverse transcriptase was used as the reaction's enzyme. During the reverse transcription reaction, a $2^{nd}$ cDNA strand was synthesized which was complementary to the $1^{st}$ cDNA strand. This $2^{nd}$ cDNA strand had the SEQ ID NO:2 on one end and its reverse complement on the other end with an mRNA sequence in the middle.

The $2^{nd}$ strand cDNA product was then used as template for a PCR reaction in which Seq. ID 2 with a 5' Cy3 or 5' Cy5 was used as the universal primer for exponential amplification.

This Cy3 or Cy5 labeled, double stranded, PCR product was then purified and concentrated to 25 uL and applied to the surface of a cDNA microarray. It was hybridized in a solution of 5×SSC and 0.2% SDS at 50° C. for 6 to 12 hours. After hybridization, the hybridized microarray was then washed in a solution of 1×SSC and 0.1% SDS for 10 minutes at 45° C. Immediately following the first wash, the microarray was washed in a second wash of 0.1×SSC and 0.2% SDS for 3 minutes at 35° C. The microarray was then scanned using an Axon Genepix 4000A microarray scanner and the hybridization pattern was detected.

EXAMPLE 2
Random Prime from polyA with Nick Translation

The cDNA microarrays were made according to U.S. Pat. No. 5,807,522 by Incyte Genomics, Inc. The oligonucleotides were synthesized and purified by Operon Technologies, and used without further purification.

The following oligonucleotide sequences were used in the execution of the example:

| | |
|---|---|
| NNNNNNNNNGTTTCCCAGTCACGATC | (SEQ ID NO:1) |
| GTTTCCCAGTCACGATC | (SEQ ID NO:2) |

The oligonucleotide of SEQ ID NO:1 was used to randomly prime a standard $1^{st}$ strand cDNA reverse transcription reaction using complex poly A purified human mRNA as template. M-MLV (RNase H+) reverse transcriptase was used as the reaction's enzyme. During the reverse transcription reaction, a $2^{nd}$ cDNA strand was synthesized which was complementary to the $1^{st}$ cDNA strand. This $2^{nd}$ cDNA strand had the SEQ ID NO:2 on one end and its reverse complement on the other end with an mRNA sequence in the middle.

The $2^{nd}$ strand cDNA product was then used as template for a PCR reaction in which Seq. ID 2 with a 5' Cy3 or 5' Cy5 was used as the universal primer for exponential amplification.

This Cy3 or Cy5 labeled, double stranded, PCR product was then purified and EtOH precipitated. This probe sample was then used as the template for nick translation. The Promega kit: Nick Translation System #U1001 was used, incorporating Cy3 or Cy5 labeled dCTP at a 4:1 cold to hot ratio.

The nick translated product was then concentrated to 25 uL and applied to the surface of a cDNA microarray. It was hybridized in a solution of 5×SSC and 0.2% SDS at 60° C. for 6 to 12 hours. After hybridization, the hybridized microarray was then washed in a solution of 1×SSC and 0.1% SDS for 10 minutes at 45° C. Immediately following the first wash, the microarray was washed in a second wash of 0.1×SSC and 0.2% SDS for 3 minutes at 25° C. The microarray was then scanned using an Axon Genepix 4000A microarray scanner and the hybridization pattern was detected.

EXAMPLE 3
Amplify from Total without Wobble

The cDNA microarrays were made according to U.S. Pat. No. 5,807,522 by Incyte Genomics, Inc. The oligonucleotides were synthesized and purified by Operon Technologies, and used without further purification.

The following oligonucleotide sequences were used in the execution of the example:

| | |
|---|---|
| ACTCAGCGTTGTTACCATTTTTTTTTTTTTTT | (SEQ ID NO:3) |
| ACTCAGCGTTGTTACCA | (SEQ ID NO:4) |
| ACTCAGCGTTGTTACCANNNNNNNNN | (SEQ ID NO:5) |

The oligonucleotide of SEQ ID NO:3 was used to prime a standard $1^{st}$ strand cDNA reverse transcription reaction using complex total RNA as template. M-MLV (RNase H+) reverse transcriptase was used as the reaction's enzyme. After the reverse transcription reaction, excess reagents were purified away and a $2^{nd}$ reverse transcription reaction was performed. Using SEQ ID NO:5, the second reverse transcription reaction generates cDNA strands which are complementary to the $1^{st}$ cDNA strand. This $2^{nd}$ cDNA strand had SEQ ID NO:4 on one end and its reverse complement on the other end with an mRNA sequence in the middle.

The $2^{nd}$ strand cDNA product was then used as template for a PCR reaction in which SEQ ID NO:4 with a 5' Cy3 or 5' Cy5 was used as the universal primer for exponential amplification. This Cy3 or Cy5 labeled, double stranded, PCR product was then purified and concentrated to 25 uL and applied to the surface of a cDNA microarray. It was hybridized in a solution of 5×SSC and 0.2% SDS at 50° C. for 6 to 12 hours. After hybridization, the hybridized microarray was then washed in a solution of 1×SSC and 0.1% SDS for 10 minutes at 45° C. Immediately following the first wash, the microarray was washed in a second wash of 0.1×SSC and 0.2% SDS for 3 minutes at 35° C. The microarray was then scanned using an Axon Genepix 4000A microarray scanner and the hybridization pattern was detected.

EXAMPLE 4
Amplify from Total RNA with Wobble

The cDNA microarrays were made according to U.S. Pat. No. 5,807,522 by Incyte Genomics, Inc. The oligonucleotides were synthesized and purified by Operon Technologies, and used without further purification.

The following oligonucleotide sequences were used in the execution of the example:

| | |
|---|---|
| ACTCAGCGTTGTTACCATTTTTTTTTTTTTTTV | (SEQ ID NO:6) |
| ACTCAGCGTTGTTACCA | (SEQ ID NO:4) |
| ACTCAGCGTTGTTACCANNNNNNNNN | (SEQ ID NO:5) |

The oligonucleotide of SEQ ID NO:3 was used to prime a standard $1^{st}$ strand cDNA reverse transcription reaction using complex total RNA as template. M-MLV (RNase H+) reverse transcriptase was used as the reaction's enzyme.

After the reverse transcription reaction, excess reagents were purified away and a $2^{nd}$ reverse transcription reaction was performed. Using SEQ ID NO:5, the second reverse transcription reaction generates cDNA strands which are complementary to the $1^{st}$ cDNA strand. This $2^{nd}$ cDNA strand had SEQ ID NO:4 on one end and its reverse complement on the other end with an mRNA sequence in the middle.

The $2^{nd}$ strand cDNA product was then used as template for a PCR reaction in which SEQ ID NO:4 with a 5' Cy3 or 5' Cy5 was used as the universal primer for exponential amplification. This Cy3 or Cy5 labeled, double stranded, PCR product was then purified and concentrated to 25 uL and applied to the surface of a cDNA microarray. It was hybridized in a solution of 5×SSC and 0.2% SDS at 50° C. for 6 to 12 hours. After hybridization, the hybridized microarray was then washed in a solution of 1×SSC and 0.1% SDS for 10 minutes at 45° C. Immediately following the first wash, the microarray was washed in a second wash of 0.1×SSC and 0.2% SDS for 3 minutes at 35° C. The microarray was then scanned using an Axon Genepix 4000A microarray scanner and the hybridization pattern was detected.

EXAMPLE 5
Amplify from polyA Pure without Wobble

The cDNA microarrays were made according to U.S. Pat. No. 5,807,522 by Incyte Genomics, Inc. The oligonucleotides were synthesized and purified by Operon Technologies, and used without further purification.

The following oligonucleotide sequences were used in the execution of the example:

| | |
|---|---|
| ACTCAGCGTTGTTACCATTTTTTTTTT-TTTTTTT | (SEQ ID NO:3) |
| ACTCAGCGTTGTTACCA | (SEQ ID NO:4) |
| ACTCAGCGTTGTTACCANNNNNNNNN | (SEQ ID NO:5) |

The oligonucleotide of SEQ ID NO:3 was used to prime a standard $1^{st}$ strand cDNA reverse transcription reaction using complex polyA purified human mRNA as template. M-MLV (RNase H+) reverse transcriptase was used as the reaction's enzyme. After the reverse transcription reaction, excess reagents were purified away and a $2^{nd}$ reverse transcription reaction was performed. Using SEQ ID NO:5, the second reverse transcription reaction generates cDNA strands which are complementary to the $1^{st}$ cDNA strand. This $2^{nd}$ cDNA strand had SEQ ID NO:4 on one end and its reverse complement on the other end with an mRNA sequence in the middle.

The $2^{nd}$ strand cDNA product was then used as template for a PCR reaction in which SEQ ID NO:4 with a 5' Cy3 or 5' Cy5 was used as the universal primer for exponential amplification. This Cy3 or Cy5 labeled, double stranded, PCR product was then purified and concentrated to 25 uL and applied to the surface of a cDNA microarray. It was hybridized in a solution of 5×SSC and 0.2% SDS at 50° C. for 6 to 12 hours. After hybridization, the hybridized microarray was then washed in a solution of 1×SSC and 0.1% SDS for 10 minutes at 45° C. Immediately following the first wash, the microarray was washed in a second wash of 0.1×SSC and 0.2% SDS for 3 minutes at 35° C. The microarray was then scanned using an Axon Genepix 4000A microarray scanner and the hybridization pattern was detected.

EXAMPLE 6
Amplify from polyA Pure with Wobble

The cDNA microarrays were made according to U.S. Pat. No. 5,807,522 by Incyte Genomics, Inc. The oligonucleotides were synthesized and purified by Operon Technologies, and used without further purification.

The following oligonucleotide sequences were used in the execution of the example:

| | |
|---|---|
| ACTCAGCGTTGTTACCATTTTTTTTTT-TTTTTTV | (SEQ ID NO:6) |
| ACTCAGCGTTGTTACCA | (SEQ ID NO:4) |
| ACTCAGCGTTGTTACCANNNNNNNNN | (SEQ ID NO:5) |

The oligonucleotide of SEQ ID NO:3 was used to prime a standard $1^{st}$ strand cDNA reverse transcription reaction using complex polyA purified human mRNA as template. M-MLV (RNase H+) reverse transcriptase was used as the reaction's enzyme. After the reverse transcription reaction, excess reagents were purified away and a $2^{nd}$ reverse transcription reaction was performed. Using SEQ ID NO:5, the second reverse transcription reaction generates cDNA strands which are complementary to the $1^{st}$ cDNA strand. This $2^{nd}$ cDNA strand had SEQ ID NO:4 on one end and its reverse complement on the other end with an mRNA sequence in the middle.

The $2^{nd}$ strand cDNA product was then used as template for a PCR reaction in which SEQ ID NO:4 with a 5' Cy3 or 5' Cy5 was used as the universal primer for exponential amplification. This Cy3 or Cy5 labeled, double stranded, PCR product was then purified and concentrated to 25 uL and applied to the surface of a cDNA microarray. It was hybridized in a solution of 5×SSC and 0.2% SDS at 50° C. for 6 to 12 hours. After hybridization, the hybridized microarray was then washed in a solution of 1×SSC and 0.1% SDS for 10 minutes at 45° C. Immediately following the first wash, the microarray was washed in a second wash of 0.1×SSC and 0.2% SDS for 3 minutes at 35° C. The microarray was then scanned using an Axon Genepix 4000A microarray scanner and the hybridization pattern was detected.

EXAMPLE 7
Amplify polyA Pure Random Onbead

The cDNA microarrays were made according to U.S. Pat. No. 5,807,522 by Incyte Genomics, Inc. The oligonucleotides were synthesized and purified by Operon Technologies, and used without further purification.

The following oligonucleotide sequences were used in the execution of the example:

| | |
|---|---|
| NNNNNNNNNGTTTCCCAGTCACGATC | (SEQ ID NO:1) |
| GTTTCCCAGTCACGATC | (SEQ ID NO:2) |

The oligonucleotide of SEQ ID NO:1 was used to randomly prime a standard $1^{st}$ strand cDNA reverse transcription reaction using complex polyA mRNA which was captured onto oligo dT/latex beads provided by the Qiagen mRNA Mini Kit. No elution of the mRNA off of the latex beads was done. M-MLV (RNase H+) reverse transcriptase was used as the reaction's enzyme. During the reverse transcription reaction, a $2^{nd}$ cDNA strand was synthesized which was complementary to the $1^{st}$ cDNA strand. This $2^{nd}$ cDNA strand had the SEQ ID NO:2 on one end and its reverse complement on the other end with an mRNA sequence in the middle.

The $2^{nd}$ strand cDNA product was then used as template for a PCR reaction in which Seq. ID 2 with a 5' Cy3 or 5' Cy5 was used as the universal primer for exponential amplification. This Cy3 or Cy5 labeled, double stranded, PCR product was then purified and concentrated to 25 uL and applied to the surface of a cDNA microarray. It was hybridized in a solution of 5×SSC and 0.2% SDS at 50° C. for 6 to 12 hours.

After hybridization, the hybridized microarray was then washed in a solution of 1×SSC and 0.1% SDS for 10 minutes at 45° C. Immediately following the first wash, the microarray was washed in a second wash of 0.1×SSC and 0.2% SDS for 3 minutes at 35° C. The microarray was then scanned using an Axon Genepix 4000A microarray scanner and the hybridization pattern was detected.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for amplifying a RNA sequence, comprising the steps of:
   (a) hybridizing to a target RNA a first primer comprising a 3' target RNA hybridizing sequence and a first 5' defined amplifiable sequence;
   (b) extending the first primer with a reverse transcriptase to form a first cDNA strand;
   (c) hybridizing to the first cDNA strand a second primer comprising a 3' random cDNA hybridizing sequence and a second 5' defined amplifiable sequence;
   (d) extending the second primer with a DNA polymerase to form a second cDNA stand; and
   (e) amplifying the second cDNA strand by a polymerase chain reaction with a third primer comprising the first 5' defined amplifiable sequence, and a fourth primer comprising the second 5' defined amplifiable sequence;
   wherein step (b) yields a heteroduplex of the target RNA and the first cDNA and further comprises the step of digesting the target RNA of the heteroduplex with a RNAse sufficient to permit hybridization of the first cDNA strand with the second primer without a melting step.

2. A method according to claim 1, wherein the 3' target RNA hybridizing sequence is random.

3. A method according to claim 1, wherein the 3' target RNA hybridizing sequence is nonrandom.

4. A method according to claim 1, wherein the 3' target RNA hybridizing sequence is nonrandom and is complementary to a predetermined sequence selected from a coding region, a poly A junction, or a poly A tail.

5. A method according to claim 1, wherein the first and second 5' defined amplifiable sequences are the same.

6. A method according to claim 1, wherein:
   the first and second 5' defined amplifiable sequences are different, and
   the method further comprises the step of functionally depleting the first primer between steps (b) and (c).

7. A method according to claim 1, wherein:
   the first and second 5' defined amplifiable sequences are different,
   the method further comprises the step of fictionally depleting the first primer between steps (b) and (c), and
   step (e) further comprises amplifying the second cDNA strand with a fourth primer comprising the second 5' defined amplifiable sequence.

8. A method according to claim 1, wherein:
   the first and second 5' defined amplifiable sequences are different,
   the method further comprises the step of functionally depleting the first primer between steps (b) and (c),
   step (e) further comprises amplifying the second cDNA strand with a fourth primer comprising the second 5' defined amplifiable sequence, and
   the method further comprises step:
     (f) amplifying the amplified cDNA with an excess of either the third or fourth primer to form a predominantly single stranded amplified probe of a predetermined orientation.

9. A method according to claim 1, wherein the method is practiced in a single tube (homogeneous).

10. A method according to claim 1, wherein the method is practiced in a single tube and the third primer and the fourth primer of step (e) are added in functional excess of the first primer.

11. A method according to claim 1, wherein the method comprises the step of functionally depleting remaining first and second primers between steps (d) and (e).

12. A method according to claim 1, wherein:
   the first and second 5' defined amplifiable sequences are the same and
   the 3' target RNA hybridizing sequence is random.

13. A method according to claim 1, wherein:
   the first and second 5' defined amplifiable sequences are the same and
   the 3' target RNA hybridizing sequence is nonrandom.

14. A method according to claim 1, wherein:
   the first and second 5' defined amplifiable sequences are the same,
   the 3' target RNA hybridizing sequence is nonrandom and
   the method is practiced in a single tube.

15. A method according to claim 1, wherein:
   the 3' target RNA hybridizing sequence is nonrandom and
   the first and second 5' defined amplifiable sequences are different and the method further comprises the step of functionally depleting the first primer between steps (b) and (c).

16. A method according to claim 1, wherein:
the 3' target RNA hybridizing sequence is nonrandom,
the first and second 5' defined amplifiable sequences are different and the method further comprises the step of functionally depleting the first primer between steps (b) and (c) and
the method is practiced in a single tube.

17. A method for amplifying a RNA sequence, comprising the steps of:
  (a) hybridizing to a target RNA a first primer comprising a 3' target RNA hybridizing sequence and a first 5' defined amplifiable sequence;
  (b) extending the first primer with a reverse transcriptase to form a first cDNA strand;
  (c) hybridizing to the first cDNA strand a second primer comprising a 3' random cDNA hybridizing sequence and a second 5' defined amplifiable sequence;
  (d) extending the second primer with a DNA polymerase to form a second cDNA strand; and
  (e) amplifying the second cDNA strand with a third primer comprising the first 5' defined amplifiable sequence;
  wherein the 3' target RNA hybridizing sequence is random;
  the first and second 5' defined amplifiable sequences are different; and
  step (b) comprises the step of functionally depleting the first primer to prevent it from hybridizing with the first cDNA strand in subsequent steps.

18. A method according to claim 17, wherein step (e) further comprises amplifying the second cDNA strand with a fourth primer comprising the second 5' defined amplifiable sequence.

19. A method according to claim 17, wherein step (e) further comprises amplifying the second cDNA strand with a fourth primer comprising the second 5' defined amplifiable sequence and the method further comprises step:
  (f) amplifying the amplified cDNA with an excess of either the third or fourth primer to form a predominantly single stranded amplified probe of a predetermined orientation.

20. A method according to claim 17, wherein step (e) further comprises amplifying the second cDNA strand with a fourth primer comprising the second 5' defined amplifiable sequence and the method further comprises step:
  (f) amplifying the amplified cDNA with an excess of either the third or fourth primer to form a predominantly single stranded amplified probe of a predetermined orientation, and
  the method is practiced in a single tube.

* * * * *

UNITED STATES PATENT AND TRADEMARK OFFICE
CERTIFICATE OF CORRECTION

PATENT NO.    : 6,379,932 B1
DATED         : April 30, 2002
INVENTOR(S)   : Arnold et al.

It is certified that error appears in the above-identified patent and that said Letters Patent is hereby corrected as shown below:

<u>Column 11,</u>
Line 36, "stand" should read -- strand --
Line 66, "fictionally" should read -- functionally --

Signed and Sealed this

Second Day of December, 2003

JAMES E. ROGAN
*Director of the United States Patent and Trademark Office*